(12) United States Patent
Chang

(10) Patent No.: US 7,871,030 B2
(45) Date of Patent: Jan. 18, 2011

(54) SPINNING REEL WITH SPOOL STEERING ARRANGEMENT

(76) Inventor: Chung-Liang Chang, 3F, No. 40, Chieh-Shou Street, Panchiao City, Taipei Hsien (TW)

( * ) Notice: Subject to any disclaimer, the term of this patent is extended or adjusted under 35 U.S.C. 154(b) by 0 days.

(21) Appl. No.: 12/627,699

(22) Filed: Nov. 30, 2009

(65) Prior Publication Data
US 2010/0133371 A1   Jun. 3, 2010

(30) Foreign Application Priority Data
Dec. 2, 2008   (TW)   ............................... 97221578 U

(51) Int. Cl.
*A01K 89/01* (2006.01)
(52) U.S. Cl. .................. 242/229; 242/249; 242/322; 242/310
(58) Field of Classification Search ................ 242/229, 242/249, 322, 310, 250, 251, 323, 241; D22/140, D22/141
See application file for complete search history.

(56) References Cited

U.S. PATENT DOCUMENTS

| | | | | |
|---|---|---|---|---|
| 1,617,543 A | * | 2/1927 | Roberts | 242/229 |
| 2,535,746 A | * | 12/1950 | Mitchell | 242/229 |
| 2,612,325 A | * | 9/1952 | Johnson | 242/229 |
| 2,613,046 A | * | 10/1952 | Redding | 242/229 |
| 2,633,307 A | * | 3/1953 | Morgan et al. | 242/229 |
| 2,749,057 A | * | 6/1956 | Jenkins et al. | 242/229 |
| 3,039,716 A | * | 6/1962 | Visockis | 242/229 |
| 3,155,340 A | * | 11/1964 | King | 242/229 |
| 3,384,320 A | * | 5/1968 | Hawk | 242/229 |
| 3,944,159 A | * | 3/1976 | Dobbs | 242/229 |
| 4,019,693 A | * | 4/1977 | Lesage | 242/229 |
| 4,106,717 A | * | 8/1978 | Thiel | 242/229 |
| 5,230,484 A | * | 7/1993 | Stevenson | 242/227 |
| 6,561,448 B2 | * | 5/2003 | Barker | 242/229 |
| 7,478,774 B2 | * | 1/2009 | Chang et al. | 242/229 |
| 2002/0027177 A1 | * | 3/2002 | Barker | 242/249 |
| 2006/0237565 A1 | * | 10/2006 | Barker | 242/229 |
| 2010/0059615 A1 | * | 3/2010 | Lombardo et al. | 242/229 |

* cited by examiner

*Primary Examiner*—Evan H Langdon
(74) *Attorney, Agent, or Firm*—Muncy, Geissler, Olds & Lowe, PLLC

(57) ABSTRACT

A spinning reel includes a holder base having two racks, an accommodation space defined between the racks and two axle holes in communication with the accommodation space at two sides, two transmission shafts respectively mounted in the axle holes, slide blocks at two sides of the holder base, a steering mechanism, which comprises two swivel brackets pivotally mounted in the accommodation space and biasable relative to each other, a skirted spool mounted in between the swivel brackets, a driving mechanism coupled to one transmission gear and adapted for rotating the skirted spool by means of a driving gear set and a rotating device coupled to the other transmission shaft and adapted for moving the slide blocks through a drive gear set and a follower gear set to force one transmission shaft into engagement with one end of the skirted spool and to bias one swivel bracket and the skirted spool between a horizontal position and a vertical position.

15 Claims, 14 Drawing Sheets

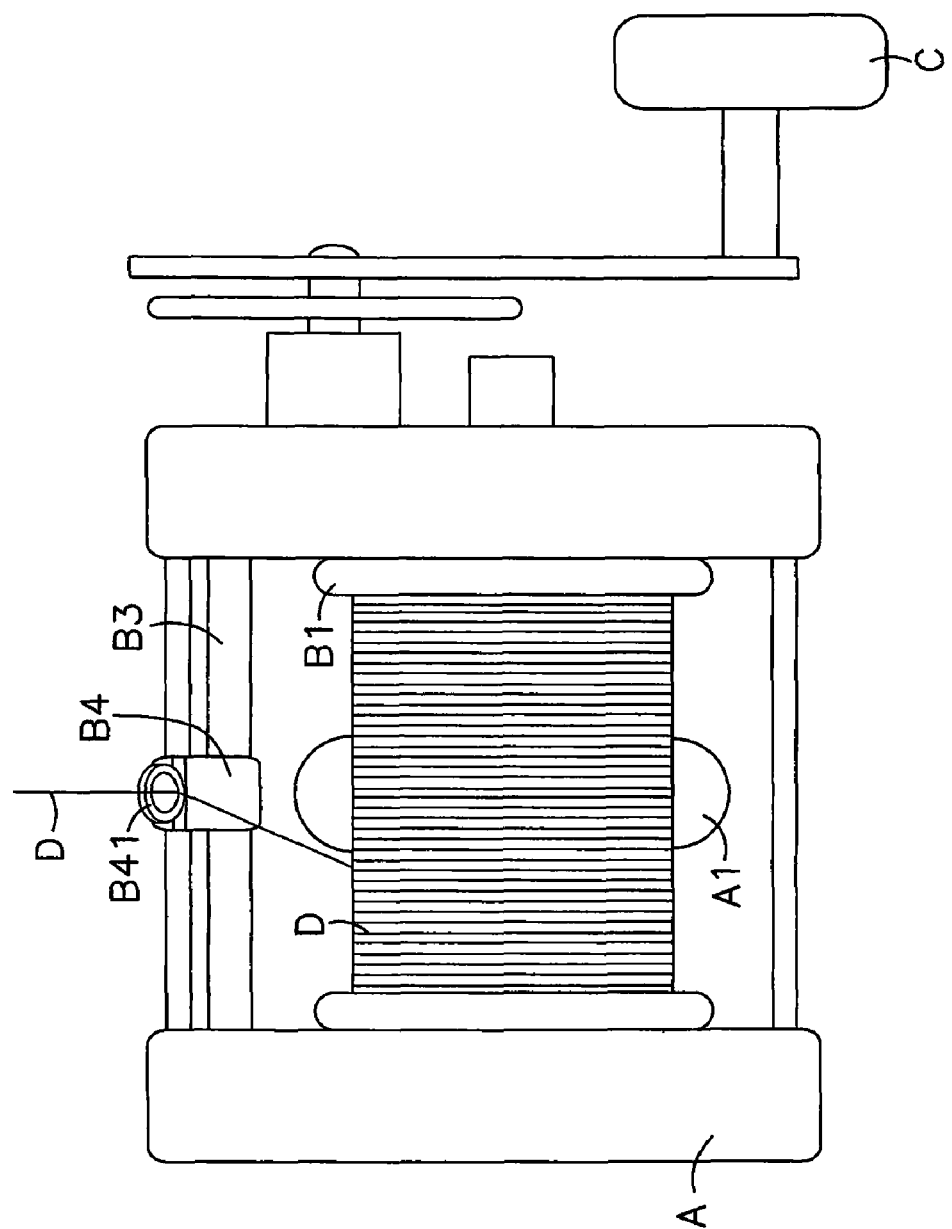

SPINNING REEL WITH SPOOL STEERING ARRANGEMENT

BACKGROUND OF THE INVENTION

This application claims the priority of Taiwan patent application number 097221578 filed on Dec. 2, 2008.

1. Field of the Invention

The present invention relates to fishing reels and more particularly a spinning reel that allows adjustment of the angle and direction of the skirted spool, enhancing the pull force when taking up the fishing line and reducing the resistance when throwing the fishing line.

2. Description of the Related Art

FIG. 13 shows a spinning reel according to the prior art. According to this design, the spinning reel comprises a base A, a reel foot A1 extended from one side of the base A for mounting on a fishing pole, a rotary bracket B pivotally disposed at the other side of the base A and supporting a skirted spool B1 in parallel to the fishing pole to which the reel foot A1 is affixed. When going to throw the fishing line, open the guide ring B2 to pull the fishing line D out of the skirted spool B1. At this time, the fishing line D does to carry the skirted spool B1 to rotate so that less resistance will be produced when throwing the fishing line D and the fishing line D can be throw out to a long distance. When taking up the fishing line, operate the handle C at the base A to rotate the rotary bracket B, causing the fishing line D to be wound on the skirted spool B1 by means of the guide of a roller B21, which guides the fishing line toward the skirted spool B1 through about 90-degrees. According to this arrangement, less pull force is produced when the fishing line D is wound on the skirted spool B1. When throwing out the fishing line D, the fishing line is not kept in straight, i.e., not kept perpendicular to the skirted spool B1, therefore the fishing line D tends to be tangled when it is being let off, affecting fishing line throwing distance.

FIG. 14 illustrates a trolling reel according to the prior art. According to this design, the trolling reel comprises a base A, a reel foot A1 provided at one side of the base A for fastening to a fishing pole, a spool B1 rotatably mounted inside the base A in a transverse direction perpendicular to the fishing pole to which the reel foot A1 is affixed. When the user manipulate the fishing pole to throw the fishing line D, the fishing line D is guided out of the spool B1 by a guide ring B41 at a slide B3 that is movable along a transverse guide rod B3 on the base A. At this time, the fishing line D pulls the spool B1 to rotate. According to this design, much resistance is produced when the user throws the fishing line D. Thus, the fishing line D cannot be rapidly pulled out of the spool B1 and thrown out to a long distance. Further, if the user stops the reel tool early, the fishing line D will be forced to jump back. If the user stops the reel too late, the spool B1 will be reversed to roll up the fishing line D due to the effect of a centrifugal force, causing tangling of the fishing line D. When wishing to take up the fishing line D, operate the handle C at the base A to rotate the spool B1, causing the fishing line D to be wound on the spool B1 subject to the guide of the guide ring B41 at the slide B3 that is moving along the transverse guide rod B3.

Therefore, there is a demand for a fishing reel that eliminates the drawbacks of the aforesaid prior art designs.

SUMMARY OF THE INVENTION

The present invention has been accomplished under the circumstances in view. It is the main object of the present invention to provide a spinning reel, which enhances the pull force when taking up the fishing line and reduces the resistance when throwing the fishing line, avoiding tangling of the fishing line.

To achieve this and other objects of the present invention, a spinning reel comprises a holder base, which comprises two racks, an accommodation space defined between the racks and two axle holes in communication with the accommodation space at two sides, two transmission shafts respectively mounted in the axle holes of the holder base, slide blocks at two sides of the holder base, a steering mechanism, which comprises two swivel brackets pivotally mounted in the accommodation space and biasable relative to each other, a skirted spool mounted in between the swivel brackets, a driving mechanism coupled to one transmission gear and adapted for rotating the skirted spool by means of a driving gear set and a rotating device coupled to the other transmission shaft and adapted for moving the slide blocks through a drive gear set and a follower gear set to force one transmission shaft into engagement with one end of the skirted spool and to bias one swivel bracket and the skirted spool between a horizontal position and a vertical position. Thus, when throwing or taking up the fishing line, the skirted spool can be biased to different angles and rotated clockwise or counter-clockwise so that a high pull force is produced when the fishing line is wound on the skirted spool and the fishing line is kept straight when it is being thrown out of the skirted spool to a long distance, avoiding tangling.

BRIEF DESCRIPTION OF THE DRAWINGS

FIG. 14 is a side view of a trolling reel according to the prior art.

DETAILED DESCRIPTION OF THE PREFERRED EMBODIMENT

Figure 1:
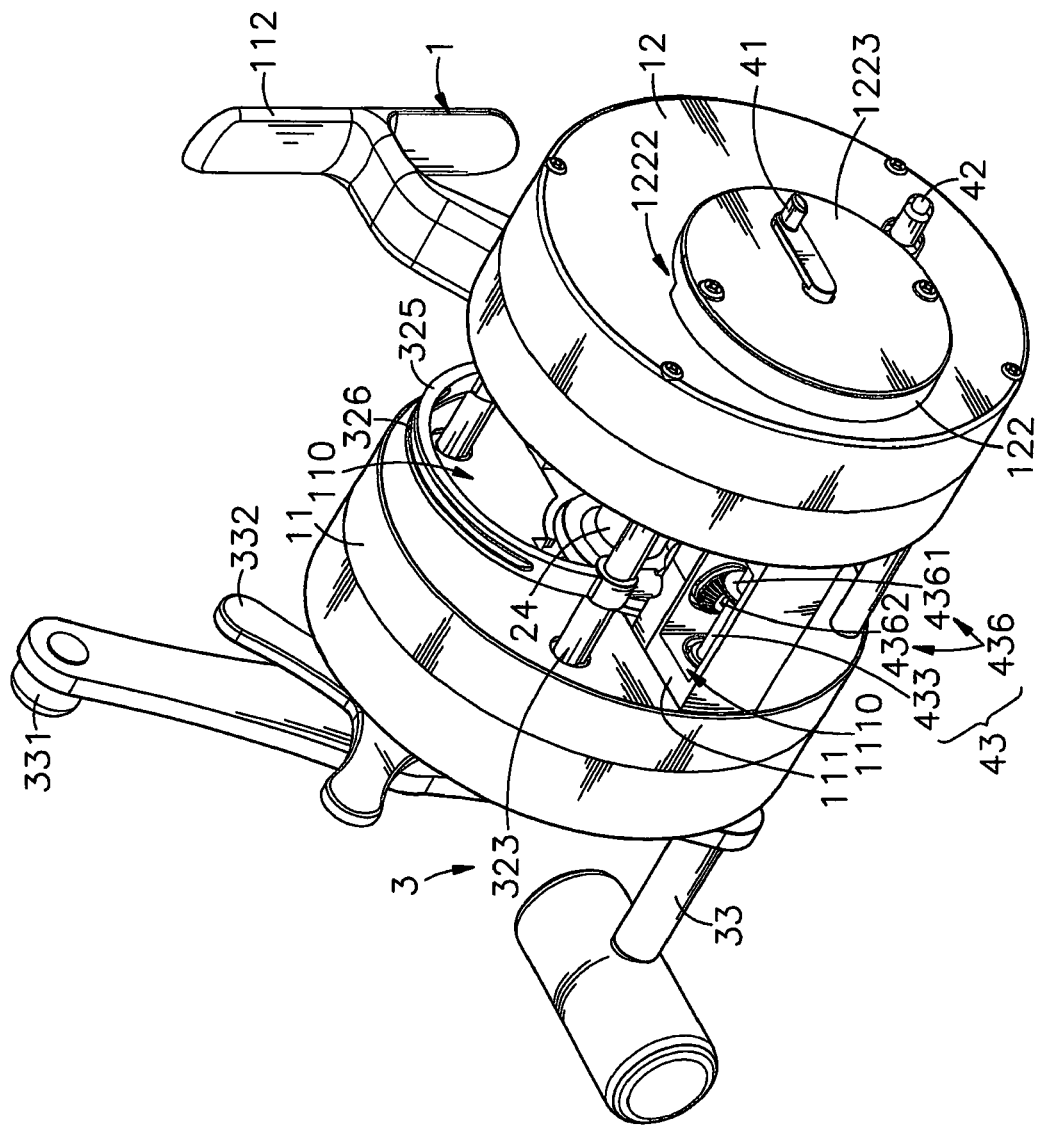
FIG. 1 is an elevational view of a spinning reel in accordance with the present invention.
Figure 2:
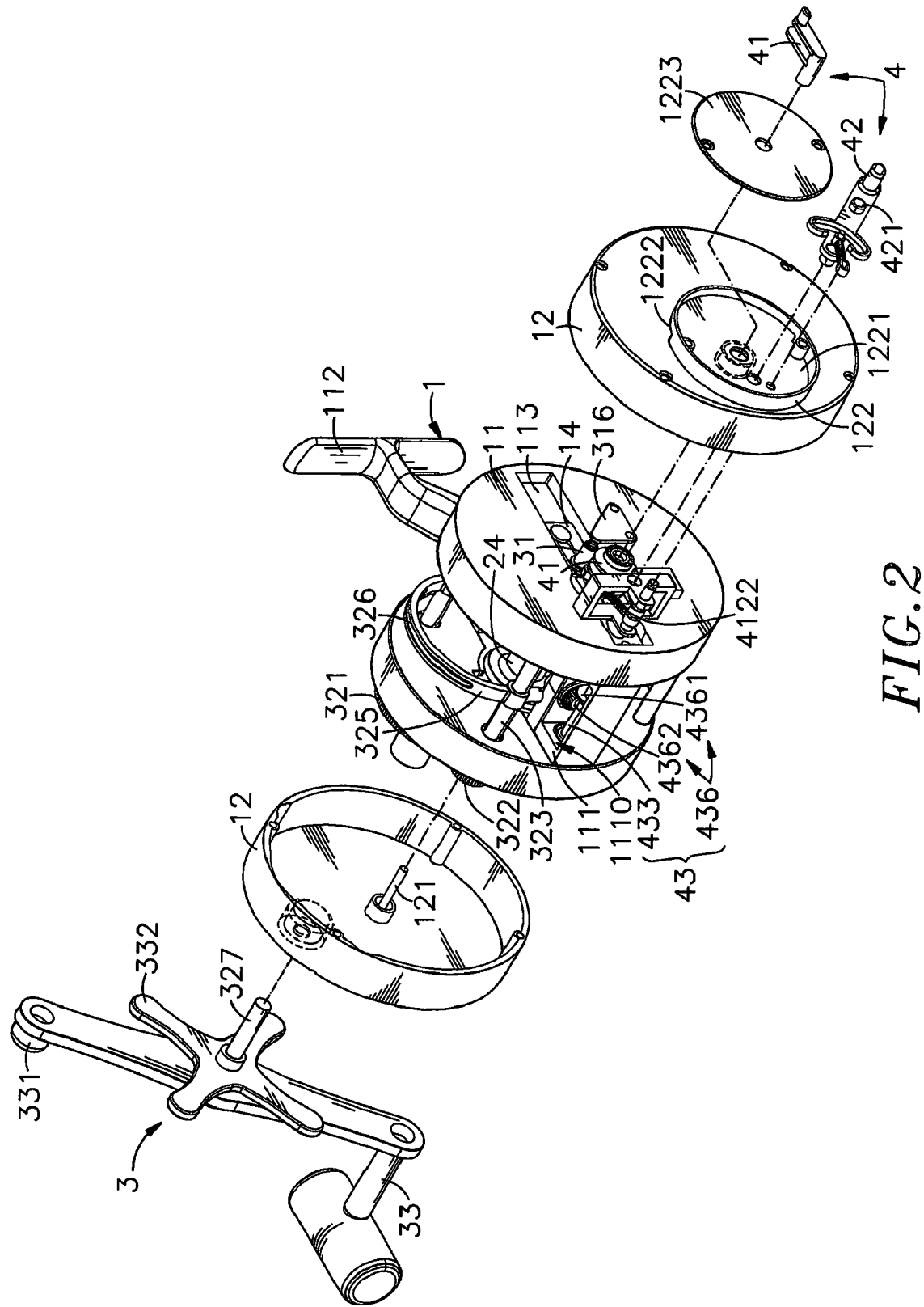
FIG. 2 is an exploded view of the spinning reel in accordance with the present invention.
Figure 3:
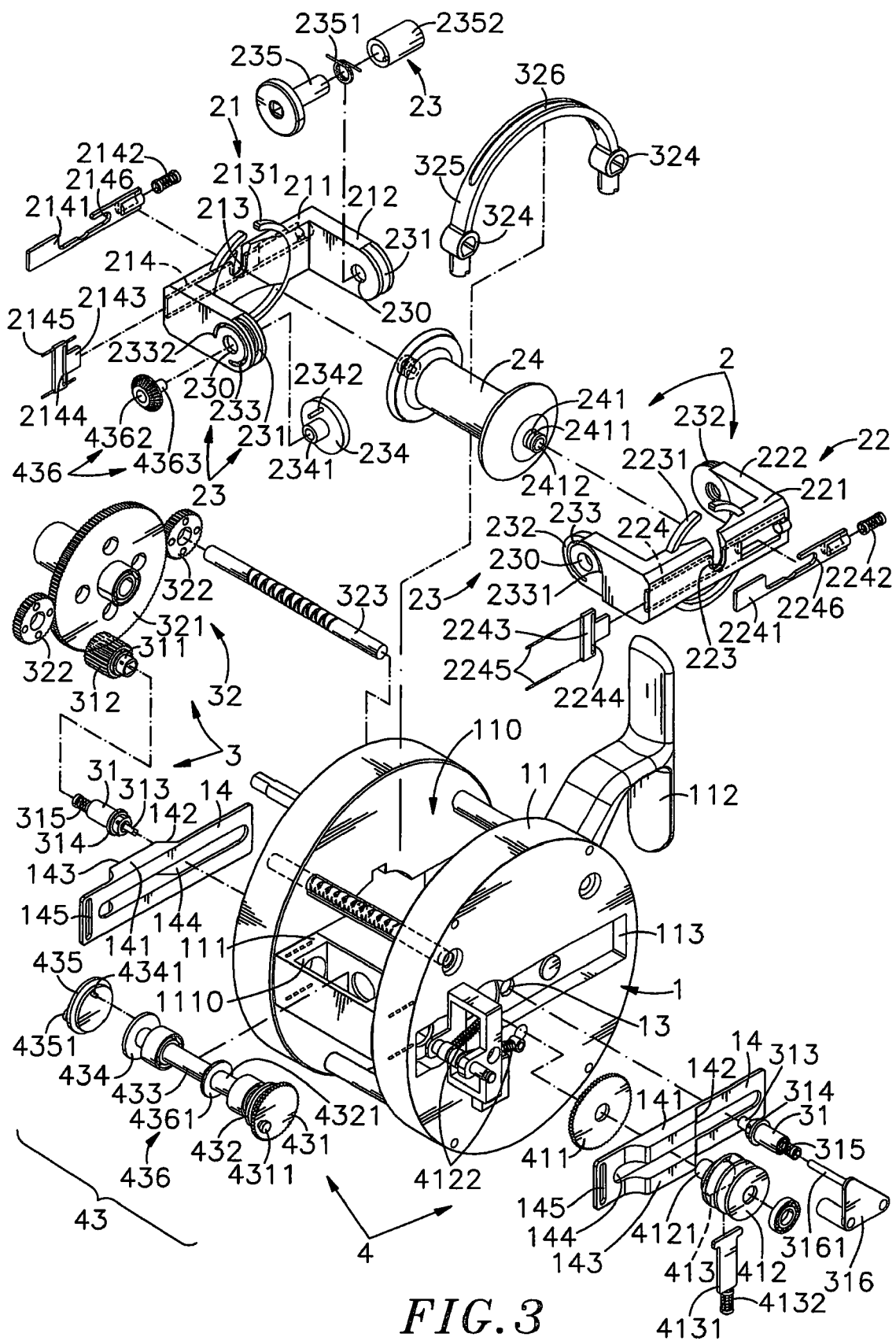
FIG. 3 is another exploded view of the spinning reel in accordance with the present invention.
Figure 4:
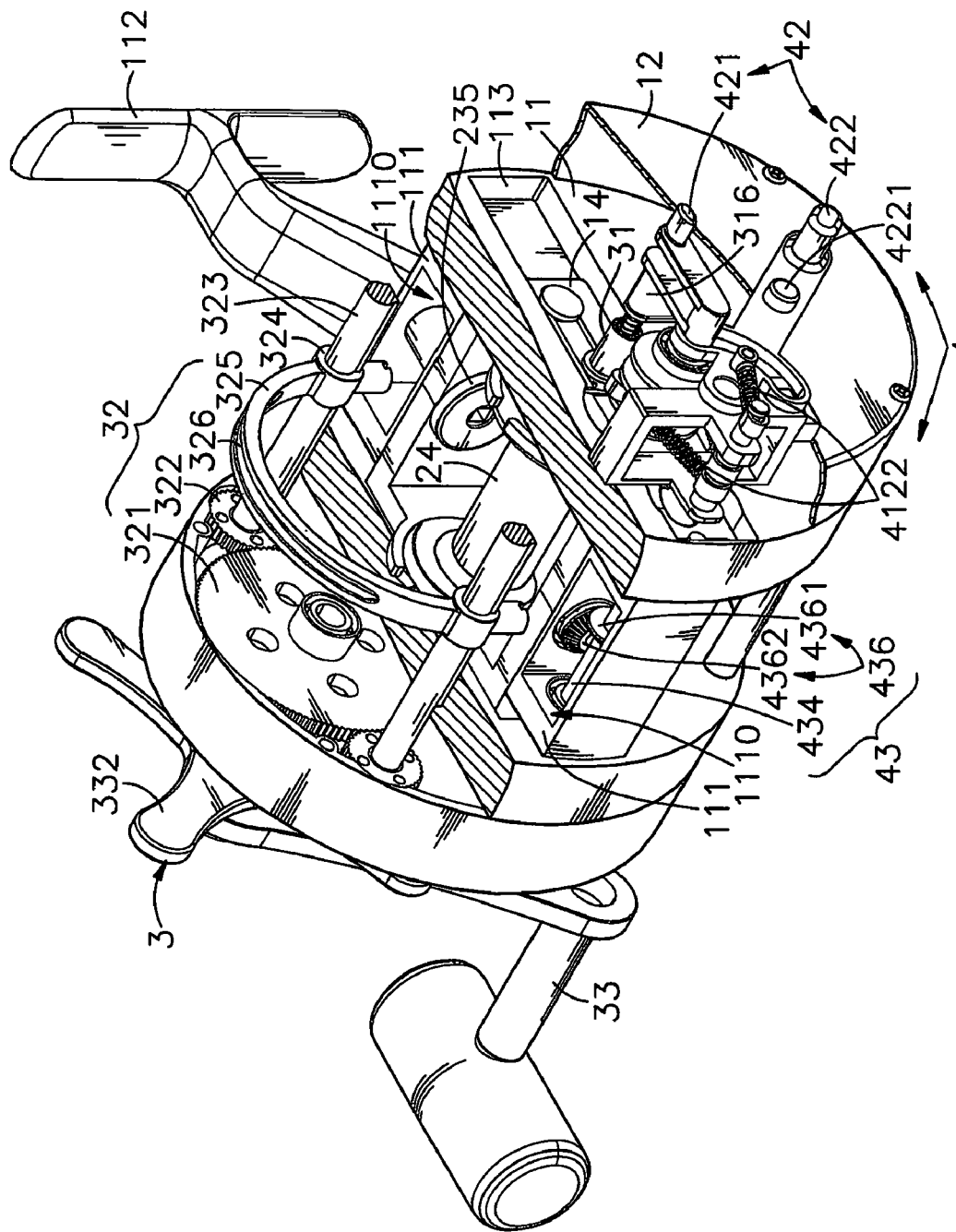
FIG. 4 is a cutaway view of the spinning reel in accordance with the present invention.
Figure 5:
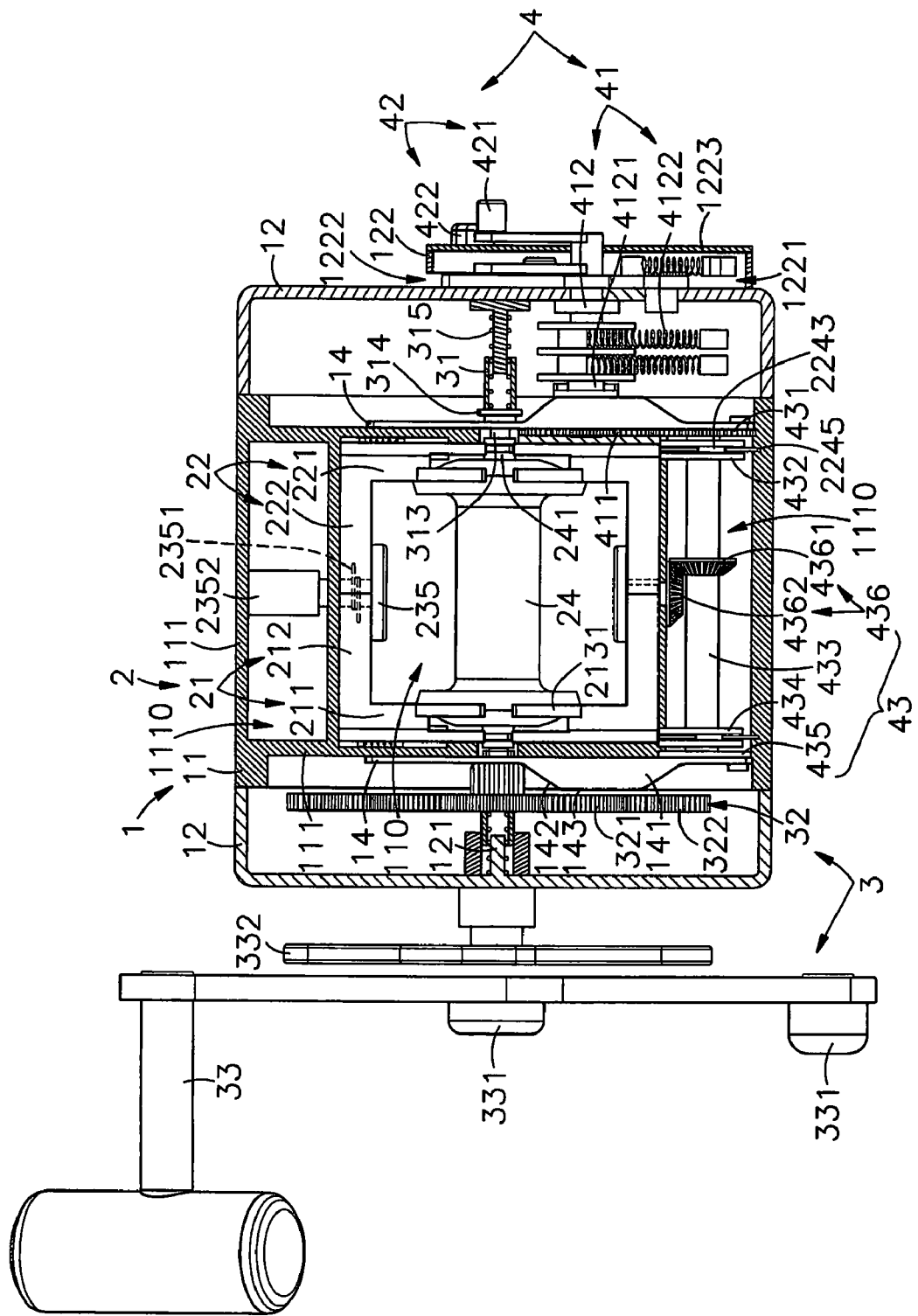
FIG. 5 is a sectional top view of the spinning reel in accordance with the present invention.
Figure 6:
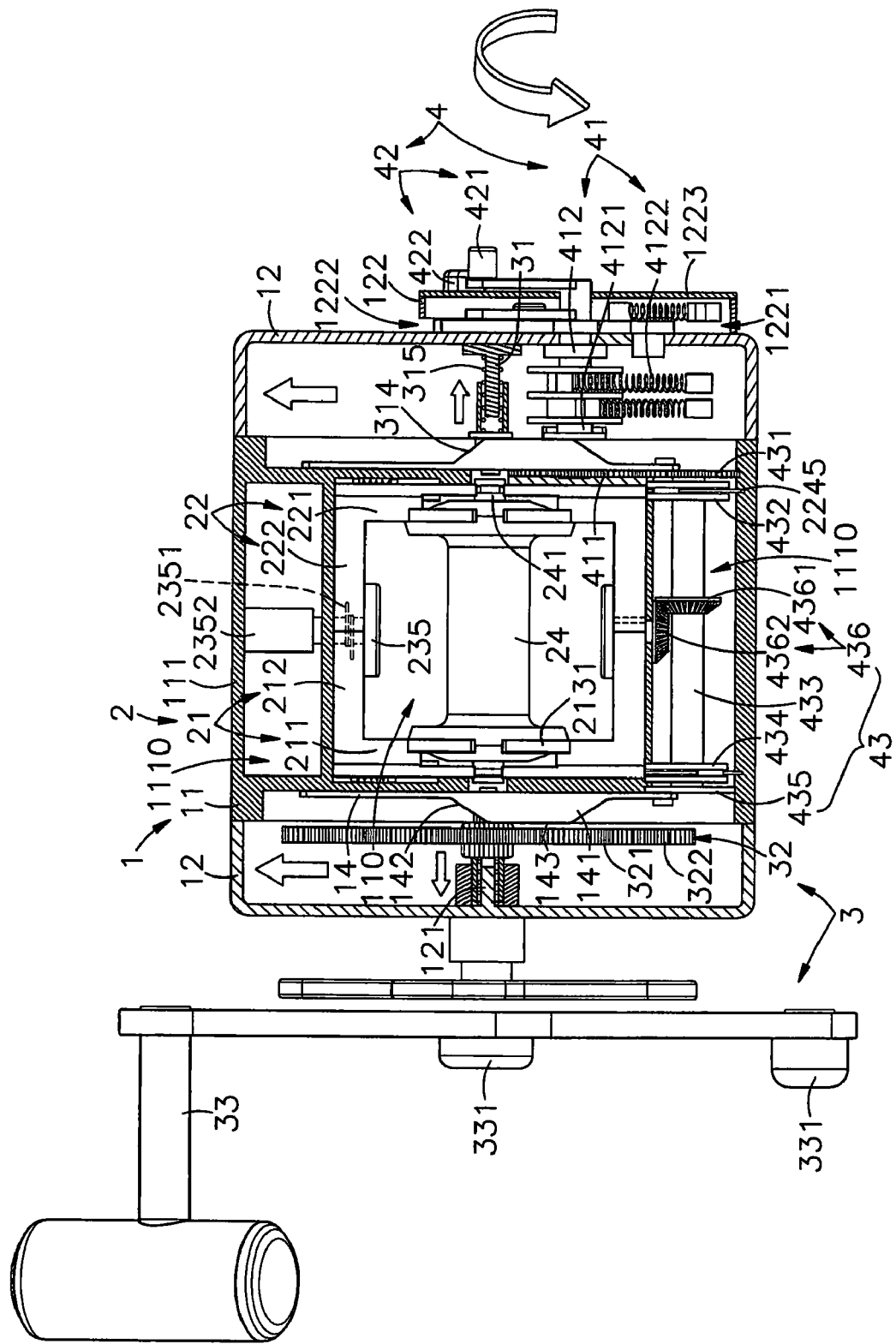
FIG. 6 corresponds to FIG. 5, showing a skirted spool direction change operation status.
Figure 7:
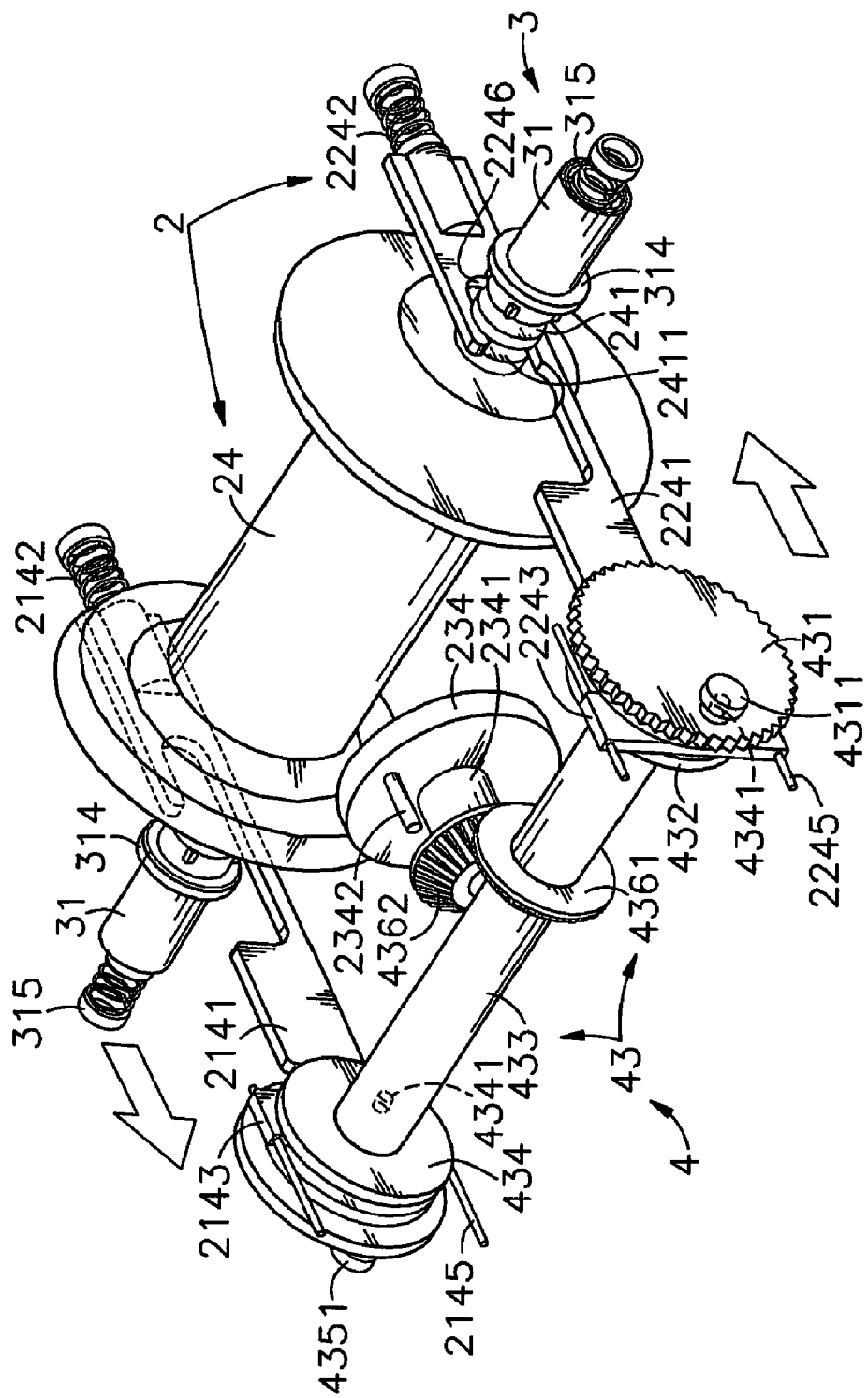
FIG. 7 is a perspective view of a part of the present invention, showing a relative motion between the rotating mechanism and the steering mechanism.

Referring to FIGS. 1~4 a spinning reel in accordance with the present invention is shown comprising a main unit 1, a steering mechanism 2, a driving mechanism 3 and a rotating mechanism 4.

The main unit 1 comprises a holder base 11 and two caps 12. The holder base 11 comprises two racks 111 respectively disposed at front and rear sides relative to an accommodation space 110 defined therein, a compartment 1110 defined in each of the two racks 111, a reel foot 112 perpendicularly outwardly extended from one of the two racks 111, a transverse sliding groove 113 externally located on each of the two opposite lateral sides thereof, an axle hole 13 located on each of the two opposite sides and respectively axially extending through the center of each transverse sliding groove 113 in communication with the accommodation space 110 and a slide block 14 slidably mounted in each of the two transverse sliding grooves 113. Each slide block 14 has a trapezoidal protrusion 141 protruded from the outer wall thereof. The trapezoidal protrusion 141 has a beveled push face 142 located on its one end, a top bearing wall 143, a transverse sliding slot 144 cut through the trapezoidal protrusion 141 in direction corresponding to the sliding direction of the transverse sliding grooves 113 and a vertical sliding slot 145 disposed adjacent to the trapezoidal protrusion 141 and extending in direction perpendicular to the extending direction of the transverse sliding slot 144. The two caps 12 are respectively capped on the two opposite lateral sides of the holder base 11, each having a positioning rod 121 for insertion into the axle holes 13 of the holder base 11 respectively, an operating zone 122 located on the outside wall, an accommodation chamber 1221 defined in the operating zone 122, a sliding way 1222 cut through the border of the operating zone 122 in communication with the accommodation chamber 1221 and a cover plate 1223 covering the accommodation chamber 1221.

The steering mechanism 2 comprises a first swivel bracket 21 and a second swivel bracket 22, two pivot joints 23 bilaterally connected between the swivel brackets 21 and 22 and a skirted spool 24 set between the first swivel bracket 21 and the second swivel bracket 22. The two swivel brackets 21 and 22 each have a base 211 or 221, two parallel arms 212 or 222 perpendicularly extended from two distal ends of the base 211 or 221, a U-notch 213 or 223 located on the middle of the base 211 or 221, two arched stop rods 2131 or 2231 extended from the base 211 or 221 at two opposite lateral sides relative to the U-notch 213 or 223, a sliding hole 214 or 224 extending through the two distal ends of the base 211 or 221 in direction perpendicular to the extending direction of the two parallel arms 212 or 222 and across the U-notch 213 or 223, a sliding strip 2141 or 2241 inserted through the sliding hole 214 or 224 and defining therein a constraint hole 2146 or 2246, a return spring 2142 or 2242 affixed to the base 211 or 221 and stopped between one end of the sliding hole 214 or 224 and one end of the sliding strip 2141 or 2241 and a push member 2143 or 2243 partially inserted into the other end of the sliding hole 214 or 224 and stopped against the other end of the sliding strip 2141 or 2241. The push member 2143 or 2243 each comprises a track 2144 or 2244, and a plurality of guide pins 2145 or 2245 slidably mounted therein. The parallel arms 212 of the first swivel bracket 21 are respectively pivotally coupled to the parallel arms 222 of the second swivel bracket 22 by the pivot joints 23. Each pivot joint 23 comprises a coupling groove 231 formed in the free end of one arm 212 of the first swivel bracket 21, a coupling tong 232 extended from the free end of one associating arm 222 of the second swivel bracket 22 and inserted into the coupling groove 231 and two pivot holes 230 respectively located on the respective arm 212 of the first swivel bracket 21 and the respective arm 222 of the second swivel bracket 22 and respectively extending across the coupling groove 231 and cut through the coupling tongue 232. One of the two pivot joints 23 further comprises two smoothly arched sliding slots 233 respectively cut through the free end of one arm 212 of the first swivel bracket 21 and the coupling tong 232 of the second swivel bracket 22 around the associating pivot holes 230 at different angles, a rotating disc 234, a pivot shaft 2341 perpendicularly extended from the center of one side of the rotating disc 234 and inserted through the two associating pivot holes 230 to pivotally secure the associating coupling tong 232 of the second swivel bracket 22 to the associating coupling groove 231 of the first swivel bracket 21 and a guide rod 2342 perpendicularly extended from the same side of the rotating disc 234 in a parallel manner relative to the pivot shaft 2341 and inserted into the two smoothly arched sliding slots 233. The other pivot joint 23 further comprises a pivot bolt 235 inserted through the two associating pivot holes 230 to pivotally secure the associating coupling tong 232 of the second swivel bracket 22 to the associating coupling groove 231 of the first swivel bracket 21 and a brake spring 2351 mounted on the pivot bolt 235 and a bush 2352 sleeved onto the pivot bolt 235. The skirted spool 24 comprises two pivot axles 241 respectively axially extended from two opposite ends thereof and respectively coupled to the U-notches 213 and 223 of the two swivel brackets 21 and 22. Each pivot axle 241 has an annular groove 2411 extending around the periphery and coupled to the constraint hole 2146 or 2246 of the sliding strip 2141 or 2241 of the swivel bracket 21 or 22, and an axial hole 2412.

The driving mechanism 3 comprises two transmission shafts 31 each having a connection pin 313 axially extended from one end thereof and a stop flange 314 extending around the periphery, a driven gear 312 having a gear shaft 311 connected to the connection pin 313 of one transmission shaft 31, a positioning member 316 having a pivot axle 3161 axially pivotally coupled to the other transmission shaft 31, two spring members 315 respectively connected between the transmission shafts 31 and the gear shaft 311 of the driven gear 312 or the positioning member 316, a driving gear set 32 and a handle 33. The driving gear set 32 comprises a driving gear wheel 321 meshed with the driven gear 312, two transmission gears 322 meshed with the driving gear wheel 321 at two opposite lateral sides, two guide rods 323 respectively perpendicularly connected to the two transmission gears 322, two barrels 324 respectively coupled to the guide rods 323, an arched connection bar 325 connected between the two barrels 324, a fishing line guide slot 326 formed in the arched connection bar 325 and a driving rod 327 perpendicularly fixedly connected to the center of the driving gear wheel 321. The handle 33 comprises a plurality of nuts 331 disposed at different locations for selectively fastening to the driving rod 327 to adjust the distance of the suspension arm between the handle 33 and the driving rod 327 and to further change the torque of the handle 33, and a lock member 332 for locking the connection between the selected nut 331 and the driving rod 327.

The rotating mechanism 4 comprises a drive gear set 41, a pull rod assembly 42 and a follower gear set 43. The drive gear set 41 comprises a drive gear 411, a drive wheel 412 having a shaft 4121 fixedly connected to the drive gear 411, a buffer wheel 413 mounted on the shaft 4121 of the drive wheel 412, a buffer spring 4132 and a buffer plate 4131 supported on the buffer spring 4132 and stopped against the periphery of the buffer wheel 413. The pull rod assembly 42 comprises a main pull rod 421 pivotally coupled to one side of the drive wheel 412 opposite to the drive gear 411, a sub pull rod 422 perpendicularly pivotally coupled to the main pull rod 421 and a push rod 4221 extended from the periphery of the sub pull rod 422. The follower gear set 43 comprises a follower gear 431 meshed with the drive gear 411 of the drive gear set 41 and having an eccentric rod 4311 perpendicularly extended from one side thereof, a follower wheel 432 connected to the other side of the follower gear 431 and having an eccentric rod 4321 perpendicularly extended from one side thereof, an axle 433 connected to the wheel center of the follower wheel 432, a driven wheel 434 connected to one end of the axle 433 remote from the follower wheel 432 and having an eccentric rod 4341 perpendicularly extended from one side thereof, a rotating wheel 435 connected to the eccentric rod 4341 of the driven wheel 434 and having an eccentric rod 4351 perpendicularly extended from one side thereof opposite to the driven wheel 434, and a transmission structure 436. The transmission structure 436 comprises a first bevel gear 4361 mounted on the axle 433, a second bevel gear 4362 meshed with the first bevel gear 4361 and a connection rod 4363 extended from the center of one side of the second bevel gear 4362 remote from the first bevel gear 4361.

During installation, accommodate the steering mechanism 2, the driving mechanism 3 and the steering mechanism 4 in the accommodation space 110 of the holder base 11 of the main unit 1, enabling the swivel brackets 21 and 22 and skirted spool 24 of the steering mechanism 2 to be pivotally mounted in the holder base 11. At this time, the respective coupling tongs 232 are respectively inserted into the respective coupling grooves 231, and then the pivot shaft 2341 of the rotating disc 234 and pivot bolt 235 are respectively inserted through the pivot holes 230 to pivotally connect the arms 212 and 222 of the swivel brackets 21 and 22 connected to the racks 111 within the accommodation space 110. Further, the guide rod 2432 of the rotating disc 234 is inserted through the arched sliding slots 233 for guiding relative movement between the swivel brackets 21 and 22 and limiting the angle of the movement. Further, the bush 2352 is sleeved onto the pivot bolt 235 and set in the compartment 1110 of one rack 111, and the brake spring 2352 is sleeved onto the pivot bolt 235 and set in the compartment 1110 connected between the pivot bolt 235 and the bush 2352. Further, the push members 2143 and 2243 are respectively coupled to the racks 111 by the respective guide pins 2145 and 2245 and respectively stopped against the associating sliding strips 2141 and 2241. Further, the pivot axles 241 of the skirted spool 24 are respectively inserted through the U-notches 213 and 223 of the swivel brackets 21 and 22 and aimed at the axle holes 13 of the holder base 11. The transmission shafts 31 are respectively inserted through the transverse sliding slots 144 of the slide blocks 14 in the transverse sliding grooves 113 of the holder base 11 and respectively pivotally mounted in the axle holes 13 of the holder base 11 to connect the respective connection pins 313 to the axial hole2 2412 of the pivot axles 241 of the skirted spool 24, keeping the respectively stop flanges 314 in contact with the top bearing walls 143 of the protrusions 141 of the respective slide blocks 14. Thereafter, the gear shaft 311 of the driven gear 312 is connected to the other end of the connection pin 313 of one transmission shaft 31 outside the holder base 11, and the driving gear wheel 321 of the driving gear set 32 is kept meshed with the driven gear 312 of the transmission gears 322, and then the guide rods 323 that are respectively connected to the transmission gears 322 are respectively inserted through the barrels 324 and mounted in the accommodation space 110 inside the holder base 11 to hold the arched connection bar 325 in the accommodation space 110 above the skirted spool 24. Thereafter, the shaft 4121 of the drive wheel 412 of the drive gear set 41 of the rotating mechanism 4 is inserted through the transverse sliding slot 144 of one slide block 14 in the associating transverse sliding groove 113 of the holder base 11 opposite to the driving gear set 32 and then connected to the drive gear 411 that is pivotally mounted in the transverse sliding groove 113 and meshed with the follower gear 431, which has its eccentric rod 4311 coupled to the vertical sliding slot 145 of the associating slide block 14. Thereafter, the eccentric rod 4321 of the follower wheel 432 is coupled to the track 2144 of the push member 2143 corresponding to the first swivel bracket 21 of the steering mechanism 2, and then the axle 433 of the follower gear set 43 is inserted into the compartment 1110 in one rack 111 of the holder base 11 to have the second bevel gear 4362 of the transmission structure 436 be pivotally connected to the pivot shaft 2341 of the rotating disc 234 by the connection rod 4363. Thereafter, the eccentric rod 4341 of the driven wheel 434 is coupled to the track 2244 of the push member 2243 corresponding to the second swivel bracket 22 of the steering mechanism 2, and then the rotating wheel 435 is mounted in the other transverse sliding groove 113 of the holder base 11 and connected to the eccentric rod 4341 of the driven wheel 434 to have its eccentric rod 4351 coupled to the transverse sliding slot 144 of the associating slide block 14. Thereafter, the two caps 12 are respectively capped on the two opposite lateral sides of the holder base 11, and the main pull rod 421 of the pull rod assembly 42 and is pivotally coupled to one side of the drive wheel 412 is inserted through the cover plate 1223 of the operating zone 122 to the outside of the main unit 1, and then the sub pull rod 422 is inserted through the sliding way 1222 to the outside of the operating zone 122, and then the driving rod 327 that is connected to the driving gear wheel 321 is inserted through the lock member 332 and fastened to one nut 331 of the handle 33. Thus, the main unit 1, the steering mechanism 2, the driving mechanism 3 and the rotating mechanism 4 are assembled, constituting the spinning reel.

According to the present preferred embodiment, the holder base 11 has two racks 111 respectively disposed at the front and rear sides relative to the accommodation space 110. In actual practice, this arrangement is not a limitation. The number and locations of the racks 111 may be changed without departing from the spirit and scope of the invention.

Further, the pivot axles 241 of the skirted spool 24 are respectively coupled to the connection pins 313 of the transmission shafts 31 of the driving mechanism 3 such that rotating the driving wheel 321 of the driving gear set 32 causes the driven gear 312 to rotate the gear shaft 311 and then the transmission shafts 31 and the skirted spool 24. The connection arrangement between the pivot axles 241 of the skirted spool 24 and the transmission shafts 31 may be made in any of a variety of other forms, allowing rotation of the skirted spool 24 subject to rotation of the driving gear set 32. Further, the transmission structure 436 may be variously embodied. Gear transmission means, linkage means, belt and pulley transmission means or the like may be used as a substitute. According to the present preferred embodiment, the transmission structure 436 is a gear transmission mechanism having the first bevel gear 4361 mounted on the axle 433 and a second bevel gear 4362 connected to the rotating disc 234 and meshed with the first bevel gear 4361. Therefore, rotating the axle 433 of the rotating mechanism 4 causes the transmission structure 436 to rotate the rotating disc 234 of the steering mechanism 2 synchronously. Other equivalent modifications and changes could be made thereunto without departing from the spirit and scope of the invention.

Referring to FIGS. 4~7, when using the spinning reel, the user can rotate the sub pull rod 422 of the pull rod assembly 42 of the rotating mechanism 4 in the counter-clockwise direction, causing the push rod 4221 to move the main pull rod 421 in the counter-clockwise direction. At this time, the tensile springs 4122 that are provided at one side of the drive wheel 412 and the buffer wheel 413, buffer plate 4131 and buffer spring 4132 that are arranged on or adjacent to the shaft 4121 impart an elastic resistance, avoiding vibration during transfer of rotating force from the shaft 4121 of the drive wheel 412 to the transmission structure 436. During rotation of the shaft 4121 of the drive wheel 412 of the drive gear set 41, the drive gear 411 is driven to rotate the follower gear 431 of the follower gear set 43, the axle 433, the rotating wheel 435 and the transmission structure 436, causing the eccentric rods 4311 of the follower gear 431 and the eccentric rod 4351 of the rotating wheel 435 to be moved in the vertical sliding slots 145 of the slide blocks 14 respectively, thereby causing the slide blocks 14 to be reciprocated in the associating transverse sliding grooves 113 of the holder base 11. At this time, the protrusions 141 of the slide blocks 14 are forced against the stop flanges 314 of the transmission shafts 31 of the driving mechanism 3 to push the transmission shafts 31 outwards relative to the holder base 11, causing the transmission shafts 31 to compress the spring members 315 at the gear shaft 311 and the positioning member 316 and also causing the connection pins 313 of the transmission shafts 31 to be disengaged from the axial holes 2412 of the pivot axles 241 of the skirted spool 24. During outward movement of the transmission shafts 31, the stop flanges 314 of the transmission shafts 31 are respectively moved along the beveled push faces 142 of the protrusions 141 to the top bearing walls 143. When the stop flanges 314 of the transmission shafts 31 reach the top bearing walls 143 of the protrusions 141 of the slide blocks 14, the transmission shafts 31 released from the constraint of the axial holes 2412 of the pivot axles 241 of the skirted spool 24.

Figure 8:
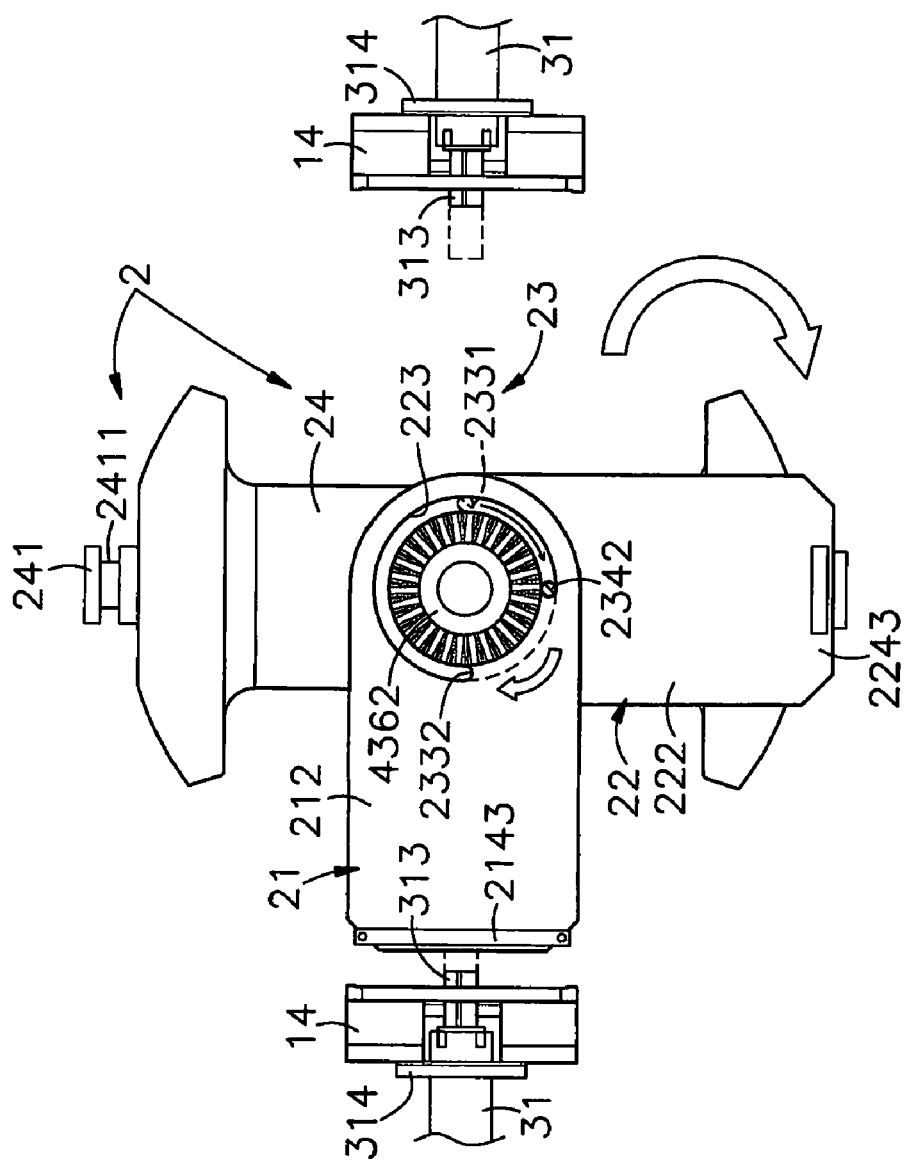
FIG. 8 is a schematic side view of a part of the present invention, showing the skirted spool turned counter-clockwise.
Figure 9:
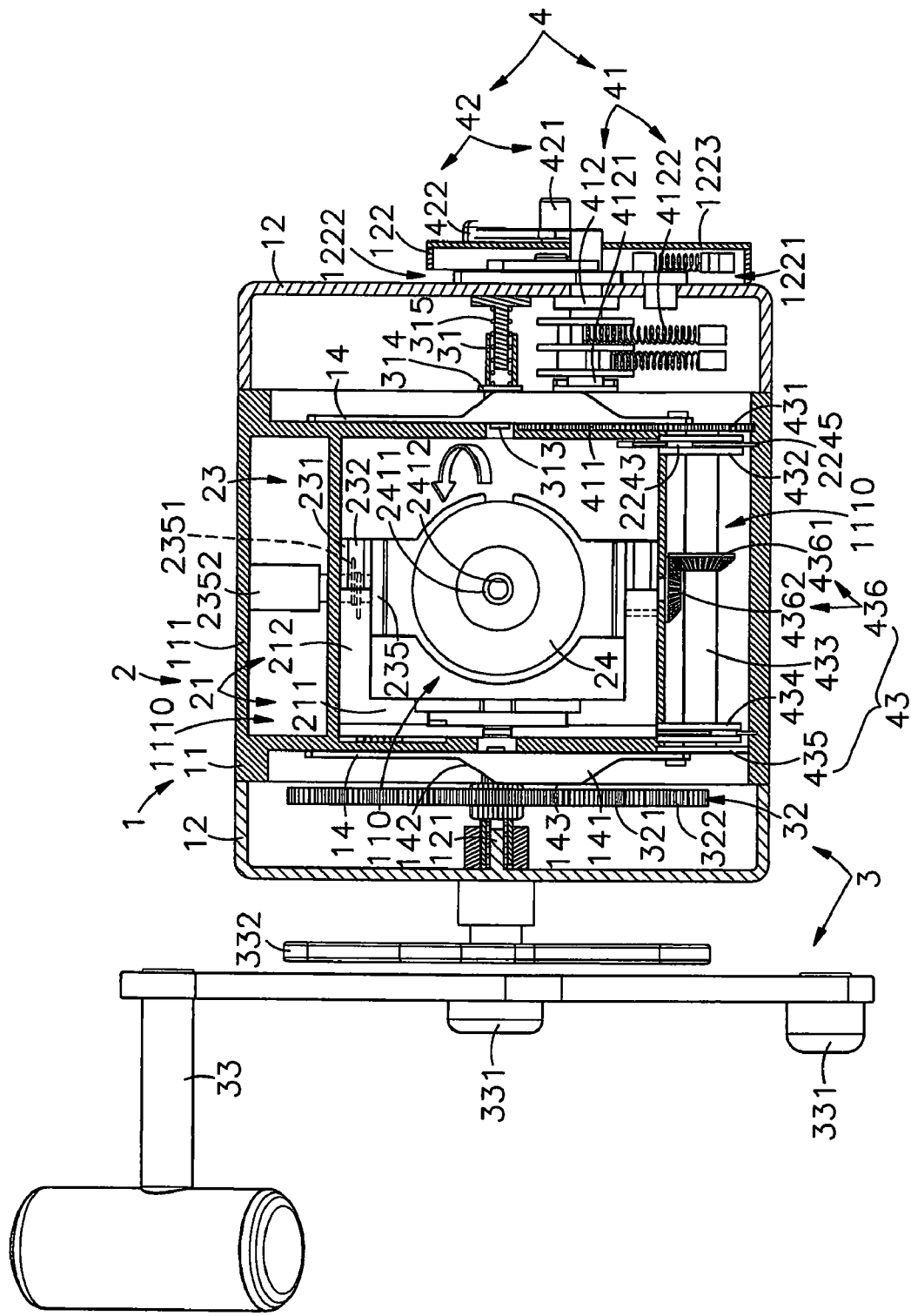
FIG. 9 is a sectional top view of the present invention, showing the skirted spool rotated in the counter-clockwise direction.

When the drive gear 411 is rotating the follower gear 431 of the follower gear set 43, the axle 433, the rotating wheel 435 and the transmission structure 436, the transmission structure 436 moves the first swivel bracket 21, causing the associating sliding strip 2141 to force its constraint hole 2146 into engagement with the annular groove 2411 of one pivot axle 241 of the skirted spool 24, thereby holding the respective pivot axle 241 in the U-notch 213 of the first swivel bracket 21. At the same time, the push member 2243 is driven by the eccentric rod 4341 of the driven wheel 434 to push the associating sliding strip 2241 in the sliding hole 224 of the second swivel bracket 22, causing the sliding strip 2241 to compress the return spring 2242 and disengage its constraint hole 2246 from the annular groove 2411 of the other pivot axle 241 of the skirted spool 24 and therefore this pivot axle 241 of the skirted spool 24 is held in the U-notch 223 of the second swivel bracket 22. Thus, when the guide rod 2342 of the rotating disc 234 is moved along the smoothly arched sliding slots 233 of the arms 212 and 222 of the swivel brackets 21 and 22 to the right limit point 2331 of the smoothly arched sliding slot 233 at the arm 222 of the second swivel bracket 22 during clockwise rotation of the rotating disc 234, the eccentric rod 4321 of the follower wheel 432 of the follower gear set 43 of the rotating mechanism 4 moves the push members 2143 and 2243, causing one pivot axle 241 of the skirted spool 23 to be disengaged from the U-notch 223 of the second swivel bracket 22. At the same time, the other pivot axle 241 of the skirted spool 23 is kept positioned in the U-notch 213 of the first swivel bracket 21, and therefore the skirted spool 24 is turned rightwards with the first swivel bracket 21 in the clockwise direction through 90-degrees from horizontal to vertical. Thereafter, the transmission structure 436 of the follower gear set 43 rotates the rotating disc 234 to move the guide rod 2342 of the rotating disc 234 along the smoothly arched sliding slots 233 of the arms 212 and 222 of the swivel brackets 21 and 22 from the right limit point 2331 of the smoothly arched sliding slot 233 at the arm 222 of the second swivel bracket 22 in the counter-clockwise direction, causing the skirted spool 24 to be turned with the first swivel bracket 21 of the steering mechanism 2 about the pivot shaft 2341 of the rotating disc 234 and the pivot bolt 235 through 90-degrees in the counter-clockwise direction from vertical to horizontal. At this time, the other pivot axle 241 of the skirted spool 24 is kept positioned in the U-notch 223 of the second swivel bracket 22, and the sliding strip 2241 in the sliding hole 224 of the second swivel bracket 22 is forced by the return spring 2242 to move the constraint hole 2246 in the U-notch 223 of the second swivel bracket 22 into engagement with the annular groove 2411 of the other pivot axle 241 of the skirted spool 24, enabling the skirted spool 24 to be returned from vertical to horizontal and received inside the accommodation space 110 in the base unit 1 (see FIGS. 8 and 9).

Figure 10:
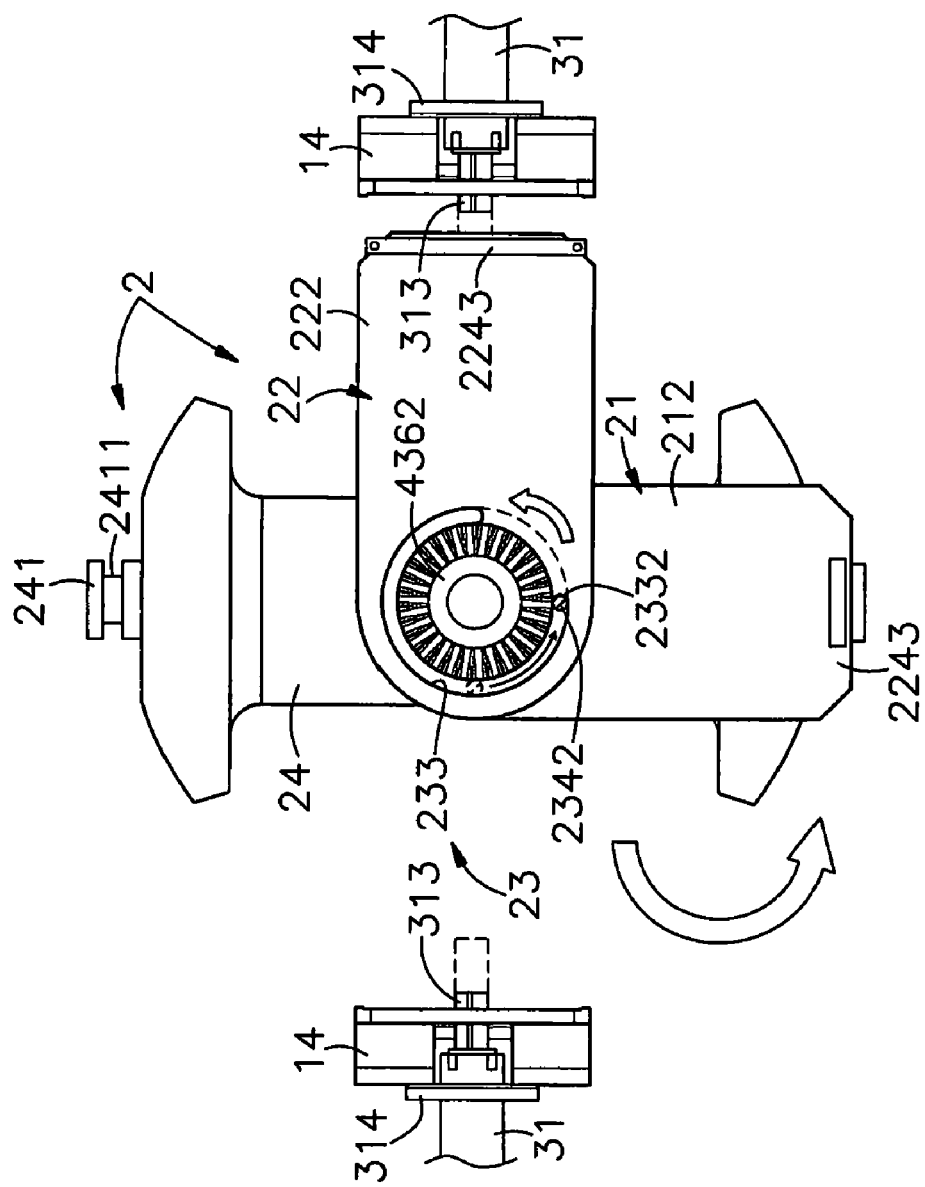
FIG. 10 is similar to FIG. 8, but showing the skirted spool turned clockwise.
Figure 11:
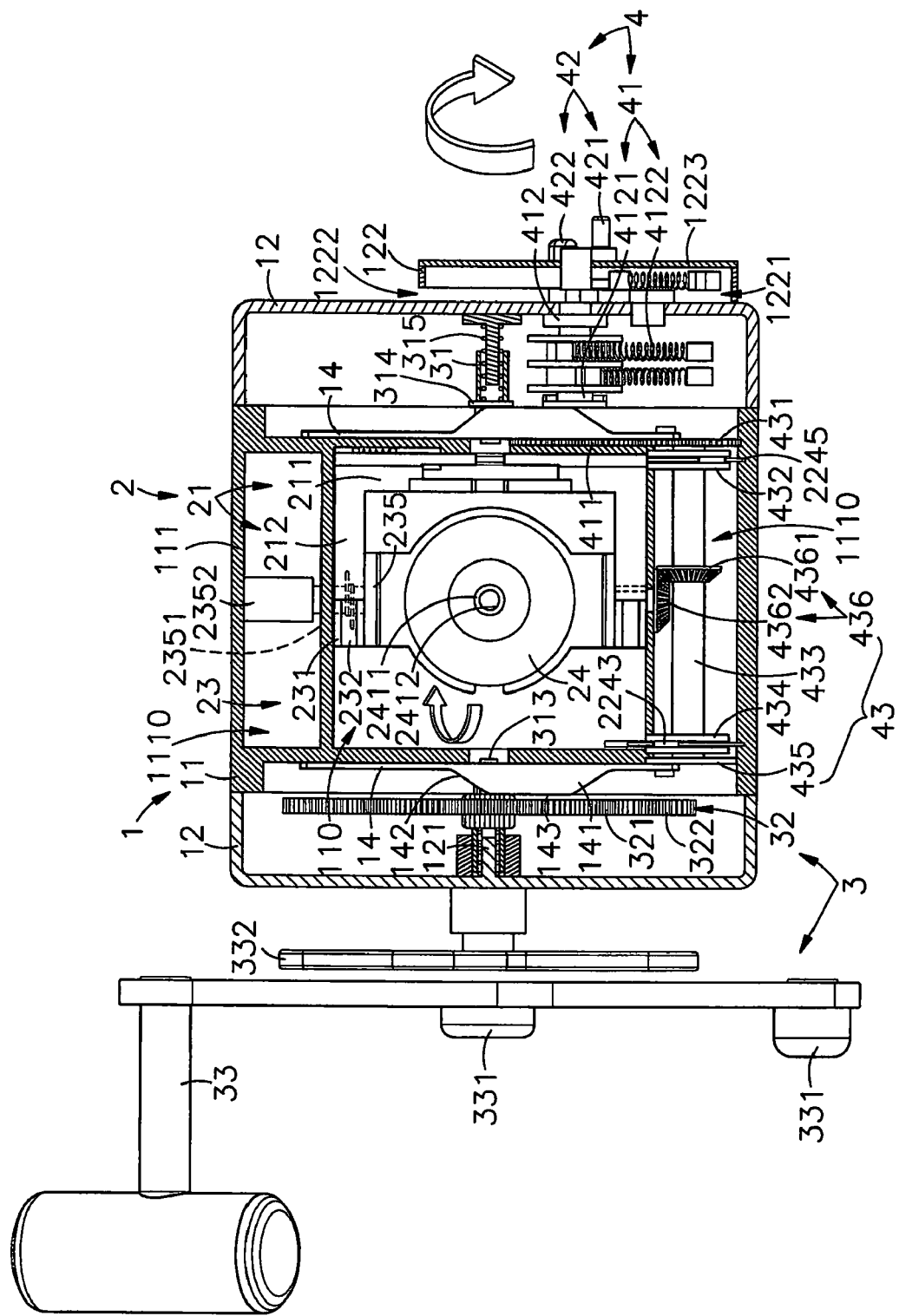
FIG. 11 is a sectional top view of the present invention, showing the skirted spool rotated in the clockwise direction
Figure 12:
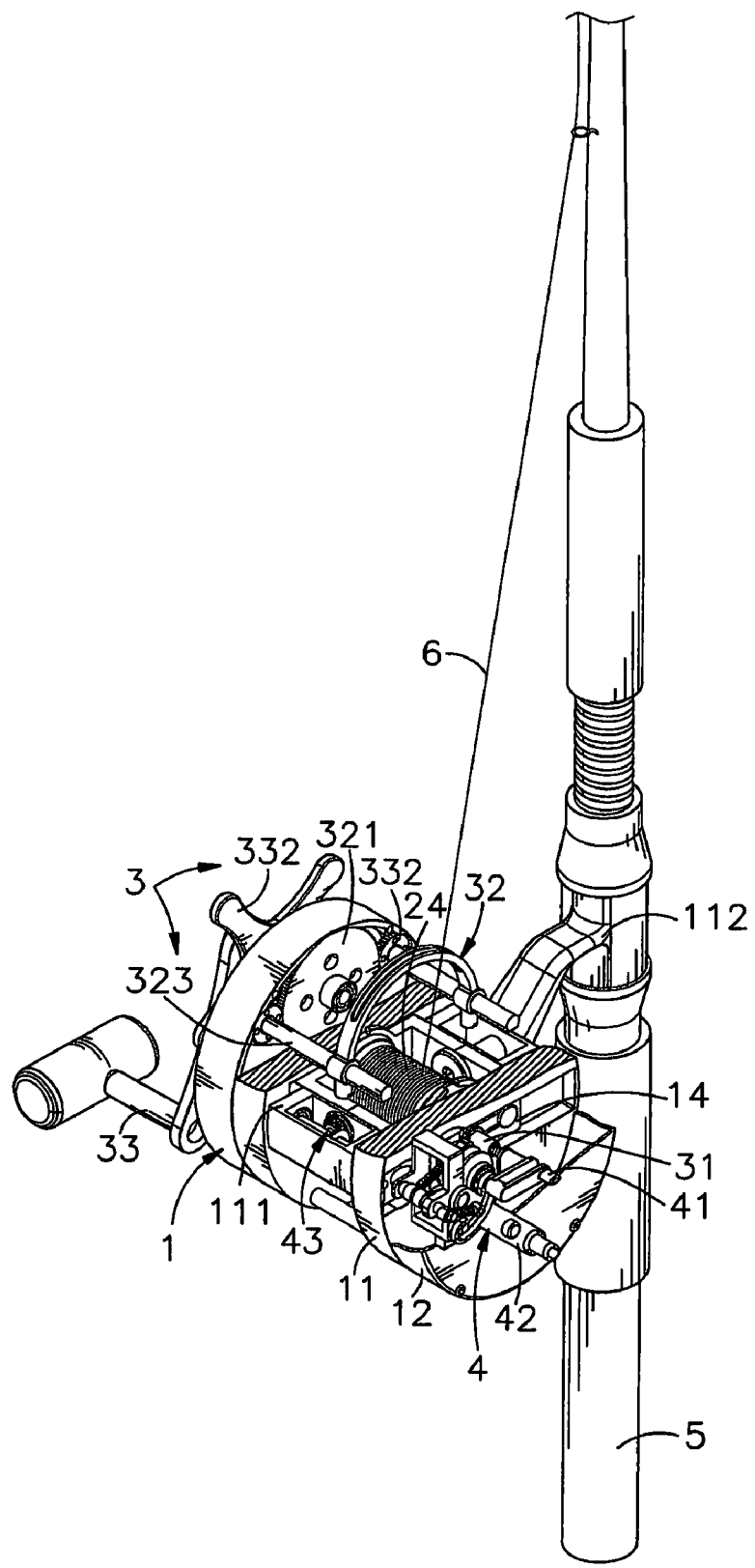
FIG. 12 is a cutaway of the present invention, showing the spinning reel fastened to a fishing pole.
Figure 13:
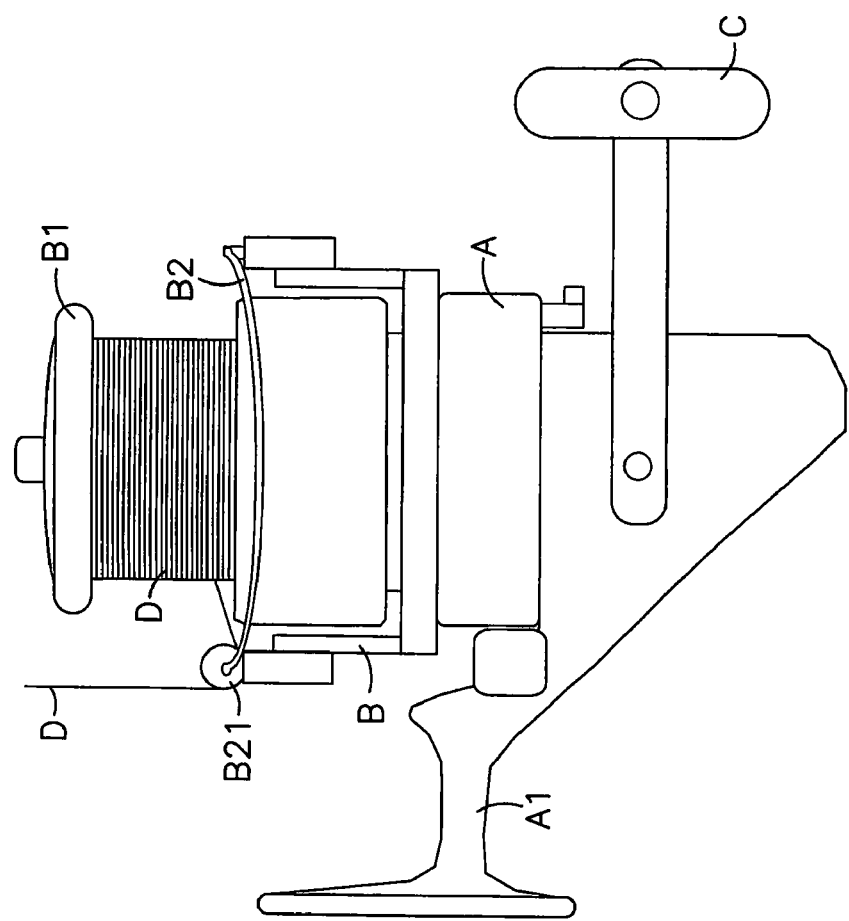
FIG. 13 is a side view of a spinning reel according to the prior art.

When the constraint hole 2246 of the sliding strip 2241 of the steering mechanism 2 is engaged with the annular groove 2411 of the associating pivot axle 241 of the skirted spool 24, the pivot axle 241 of the skirted spool 24 is held in the U-notch 223 of the second swivel bracket 22. At this time, the push member 2143 is driven by the eccentric rod 4321 of the follower wheel 432 to move the sliding strip 2141 in the sliding hole 214 of the first swivel bracket 21 against the return spring 2142, thereby disengaging the constraint hole 2146 of the sliding strip 2141 from the annular groove 2411 of the associating pivot axle 241 of the skirted spool 24, and therefore the respective pivot axle 241 of the skirted spool 24 is positioned in the U-notch 223 of the second swivel bracket 22. Thereafter, the guide rod 2342 of the rotating disc 234 is moved along the smoothly arched sliding slots 233 of the arms 212 and 222 of the swivel brackets 21 and 22 to the left limit point 2332 of the smoothly arched sliding slot 233 at the arm 222 of the second swivel bracket 22 during counter-clockwise rotation of the rotating disc 234, the eccentric rod 4321 of the follower wheel 432 of the follower gear set 43 of the rotating mechanism 4 moves the push members 2143 and 2243, causing one pivot axle 241 of the skirted spool 23 to be disengaged from the U-notch 213 of the first swivel bracket 21. At the same time, the other pivot axle 241 of the skirted spool 23 is kept positioned in the U-notch 223 of the first swivel bracket 22, and therefore the skirted spool 24 is turned leftwards with the second swivel bracket 22 in the counter-clockwise direction through 90-degrees from horizontal to vertical. Thereafter, the transmission structure 436 of the follower gear set 43 rotates the rotating disc 234 to move the guide rod 2342 along the smoothly arched sliding slots 233 of the arms 212 and 222 of the swivel brackets 21 and 22 from the left limit point 2332 of the smoothly arched sliding slot 233 at the arm 212 of the first swivel bracket 22 in the clockwise direction, causing the skirted spool 24 to be turned with the second swivel bracket 22 of the steering mechanism 2 about the pivot shaft 2341 of the rotating disc 234 and the pivot bolt 235 through 90-degrees in the clockwise direction from vertical to horizontal. At this time, the other pivot axle 241 of the skirted spool 24 is kept positioned in the U-notch 213 of the first swivel bracket 21, and the sliding strip 2141 in the sliding hole 214 of the first swivel bracket 21 is forced by the return spring 2142 to move the constraint hole 2146 in the U-notch 213 of the first swivel bracket 21 into engagement with the annular groove 2411 of the associating pivot axle 241 of the skirted spool 24, enabling the skirted spool 24 to be returned from vertical to horizontal and received inside the accommodation space 110 in the base unit 1 (see FIGS. 10 and 11).

Further, the brake spring 2351 mounted on the pivot bolt 235 and connected between the pivot bolt 235 and the second swivel bracket 22 to provide a return force to the second swivel bracket 22, stabilizing reversing displacement of the second swivel bracket 22.

Referring to FIGS. 8~12, the reel foot 112 of the holder base 11 of the base unit 1 is affixed to a fishing pole 5. When the user uses the fishing pole 5 to catch fish and to throw the fishing line 6, the user can rotate the pull rod assembly 42 of the steering mechanism 4 in the counter-clockwise direction to rotate the steering mechanism 2 and the skirted spool 24 leftwards through 90-degrees or in the clockwise direction to turn the steering mechanism 2 and the skirted spool 24 rightwards through 90-degrees, allowing the skirted spool 24 to be skirted spool 24 to be turned leftwards or rightwards into vertical in parallel to the fishing pole 5, facilitating throwing of the fishing line 6 that is wound on the skirted spool 24 and extends through the fishing line guide slot 326 of the arched connection bar 325. When the user turns the fishing pole 5 backwards before throwing out the fishing line 6, the fishing line 6 does not move the skirted spool 24, and therefore the fishing line 6 can be pulled out of the skirted spool 24 and thrown out to a far distance rapidly with less resistance.

When going to take up the fishing line 6, the user can rotate the pull rod assembly 42 in the clockwise or counter-clockwise direction to turn the steering mechanism 2 and the skirted spool 24 rightwards or leftwards through 90-degrees to a transverse (horizontal) position substantially perpendicular to the fishing pole 5, and then operate the handle 33 of the driving mechanism 3 to rotate the skirted spool 24, thereby causing the skirted spool 24 to take up the fishing line 6 through the fishing line guide slot 326 of the arched connection bar 325. During the fishing line take-up operation, the fishing line 6 and the skirted spool 24 are synchronously moved, causing the fishing line 6 to be wound round the skirted spool 24 smoothly and evenly, avoiding fishing line tangling or uneven winding of the fishing line 6 on the skirted spool 24. Thus, the fishing line 6 is evenly wound on the skirted spool 24 in a high pulling resistance manner, facilitating further throwing action (see FIG. 12).

Therefore, the main feature of the present invention is that the steering mechanism 2 is mounted in the holder base 11 of the base unit 1 to have the arms 212 and 222 of the two swivel brackets 21 and 22 be pivotally coupled to the two racks 111 by the pivot shaft 2341 of the rotating disc 234 and the pivot bolt 235 within the accommodation space 110; the transmission shafts 31 of the driving mechanism 3 are respectively inserted through the transverse sliding slots 144 of the slide blocks 14 and the transverse sliding grooves 113 and axle holes 13 of the holder base 11 and moved into engagement with or away from the skirted spool 24 of the steering mechanism 2; the driving gear set 32 of the driving mechanism 3 is meshed with the driven gear 312 that has its gear shaft 311 connected to one transmission shaft 31 for enabling the driving mechanism 3 to rotate the skirted spool 24; the shaft 4121 of the drive wheel 412 of the rotating mechanism 4 extends through the transverse sliding slot 144 of one slide block 14 to the outside of the holder base 11, and the axle 433 of the follower gear set 43 extends out of the left and right sides of the holder base 11 for enabling the eccentric rod 4311 of the follower gear 431 and the eccentric rod 4351 of the rotating wheel 435 to be respectively inserted through the vertical sliding slots 145 of the slide blocks 14 and the transmission structure 436 of the follower gear set 43 to be coupled to the pivot shaft 2341 of the rotating disc 234 that pivotally couples one arm 212 of the first swivel bracket 21 and one associating arm 222 of the second swivel bracket 22 so that the transmission structure 436 can be driven to bias the steering mechanism 2 and the skirted spool 24 in different directions to let the skirted spool 24 be rotated in the vertical or transverse (horizontal) position.

In conclusion, the spinning reel of the present invention has the following advantages:

When the user rotate the pull rod assembly 42 of the rotating mechanism 4 in the clockwise or counter-clockwise direction, the drive gear set 41 rotates the transmission structure 436 of the follower gear set 43 to bias the skirted spool 24 and the first swivel bracket 21 or second swivel bracket 21 in the leftward or rightward direction through 90-degrees between a vertical position and a transverse (horizontal) position. Thus, when the user manipulates the fishing pole 5 to throw the fishing line 6, the skirted spool 24 can be turned from horizontal to vertical, lowering the resistance. On the contrary, when the user operates the spinning reel to take up the fishing line 6, the skirted spool 24 can be turned from vertical to horizontal, enabling the fishing line 6 to be wound on the skirted spool 24 evenly and smoothly.

What the invention claimed is:

1. A spinning reel, comprising:
a base unit, said base unit comprising a holder base, said holder base comprising two racks respectively disposed at front and rear sides thereof, an accommodation space defined between said two racks and two axle holes axially aligned at left and right sides thereof, two transmission shafts respectively axially movably mounted in said axle holes and two slide blocks respectively arranged on the left and right sides of said holder base and movable back and forth relative to said holder base to move said transmission shafts axially in said axle holes between an engaging position and a disengaging position, each said slide block comprising a transverse sliding slot for the passing of said transmission shafts;
a steering mechanism, said steering mechanism comprising a first swivel bracket and a second swivel bracket pivotally mounted in said accommodation space inside said holder base and biasable relative to each other, said first swivel bracket and said second swivel bracket each comprising a U-notch located on a middle part thereof, and a skirted spool set between said first swivel bracket and said second swivel bracket for the winding of a fishing line and biasable with one for said first swivel bracket and said second swivel bracket relative to the other of said first swivel bracket and said second swivel bracket between a horizontal position and a vertical position, said skirted spool comprising two pivot axles respectively extended from two opposite ends thereof for positioning in the U-notch of said first swivel bracket and the U-notch of said second swivel bracket respectively, each said pivot axle of said skirted spool having an axial hole for the engagement of one said transmission shaft to hold the associating pivot axle of said skirted spool in the U-notch of one of said first swivel skirt and said second swivel skirt;
a driving mechanism, said driving mechanism comprising a driving gear set and a gear shaft rotatable by said driving gear set, said gear shaft being connectable to one said transmission shaft for enabling said skirted spool to be rotated by said driving gear set, and a driving gear set adapted to rotate said gear shaft; and a rotating mechanism pivotally mounted in said holder base adjacent to one side of the other said transmission shaft, said rotating mechanism comprising a drive gear set, a pull rod assembly for rotating said drive gear set and a follower gear set meshed with said drive gear set and adapted to reciprocate said slide blocks in moving said transmission shafts for biasing said first swivel brackets, said second swivel bracket and said skirted spool.

2. The spinning reel as claimed in claim 1, wherein said base unit comprises a reel foot perpendicularly outwardly extended from one said rack of said holder base for mounting on a fishing pole.

3. The spinning reel as claimed in claim 1, wherein said holder base comprises two transverse sliding grooves respectively located on the left and right sides corresponding to the axle holes thereof for guiding sliding movement of said slide blocks; each said slide block comprises two protrusions disposed at two opposite lateral sides of the transverse sliding slot thereof and a vertical sliding slot disposed at one side relative to the transverse sliding slot thereof and coupled to one of said drive gear set and said follower gear set of said rotating mechanism.

4. The spinning reel as claimed in claim 3, wherein said follower gear set of said rotating mechanism comprises and axle rotatably inserted through the left and right sides of said holder base into the transverse sliding grooves of said holder base, a follower gear fixedly mounted on one end of said axle and meshed with said drive gear set, said follower gear comprising an eccentric rod perpendicularly extended from one side thereof and disposed in one transverse sliding groove of said holder base and coupled to one said slide block and a rotating wheel fixedly mounted on an opposite end of said axle and disposed in the other transverse sliding groove of said holder base, said rotating wheel comprising an eccentric rod perpendicularly extended from one side thereof and coupled to the other said slide block.

5. The spinning reel as claimed in claim 3, wherein each protrusion of each slide block has a top bearing wall for supporting the associating transmission shaft in said disengaging position and a beveled push face located on one end of said top bearing wall for moving the associating transmission shaft between said engaging position and said disengaging position.

6. The spinning reel as claimed in claim 1, wherein said first swivel bracket and said second swivel bracket each comprise a base and two parallel arms respectively perpendicularly extended from two distal ends of said base, each said arm having a pivot hole on the free end thereof, one arm of each of said first swivel bracket and said second swivel bracket comprising a smoothly arched sliding slot extending around the pivot hole of the respective arm; said steering mechanism further comprises a rotating disc inserted through the pivot hole of one arm of each of said first swivel bracket and said second swivel bracket and pivotally connected to one said rack of said holder base for rotation by said rotating mechanism and a pivot bolt inserted through the pivot hole of the other arm of each of said first swivel bracket and said second swivel bracket and pivotally connected to the other said rack of said holder base, said rotating disc comprising a guide rod coupled to the smoothly arched sliding slot on one arm of each of said first swivel bracket and said second swivel bracket for biasing one of said first swivel bracket and said second swivel bracket relative to the other of said first swivel bracket and said second swivel bracket upon rotation of said rotating disc.

7. The spinning reel as claimed in claim 1, wherein said steering mechanism further comprises a first pivot joint adapted to pivotally coupled one arm of each of said first swivel bracket and said second swivel bracket to one said rack of said holder base and a second pivot joint adapted to pivotally coupled the other arm of each of said first swivel bracket and said second swivel bracket to the other said rack of said holder base, said first pivot joint comprising a pivot bolt about which said first swivel bracket and said second swivel bracket are turned and a brake spring acting upon said pivot bolt, said second pivot joint comprising a rotating disc and a pivot shaft fixedly perpendicularly extended from one side of said rotating disc and pivotally inserted through one arm of each of said first swivel bracket and said second swivel bracket and one said rack of said holder base and coupled to a transmission structure of said rotating mechanism.

8. The spinning reel as claimed in claim 1, wherein said pull rod assembly comprises a main pull rod and a sub pull rod coupled to said main pull rod, said main pull rod being connected to said drive gear set, said sub pull rod being connected to said follower gear set; said follower gear set comprises an axle and a transmission structure mounted on said axle for rotating said steering mechanism upon rotation of said axle.

9. The spinning reel as claimed in claim 8, wherein said transmission structure comprises a first bevel gear mounted on said axle and a second bevel gear meshed with said first bevel gear and coupled to said steering mechanism.

10. The spinning reel as claimed in claim 8, wherein said drive gear set comprises a drive gear connected to said main pull rod, a buffer wheel mounted between said drive gear and said main pull rod, and a spring-supported buffer plate stopped against said buffer wheel.

11. The spinning reel as claimed in claim 1, wherein said first swivel bracket and said second swivel bracket each comprise two arched stop rods extended from the base thereof at two opposite lateral sides relative to the U-notch thereof for guiding winding of a fishing line on said skirted spool.

12. The spinning reel as claimed in claim 11, wherein said first swivel bracket and said second swivel bracket each further comprise a sliding hole extending through two distal ends of the base across the U-notch thereof, a sliding strip inserted through said sliding hole and defining therein a constraint hole, a return spring affixed to the base thereof and stopped between one end of said sliding hole and one end of said sliding strip and a push member partially inserted into the other end of said sliding hole and movable by said follower gear set to move said sliding strip in said sliding hole.

13. The spinning reel as claimed in claim 1, wherein said driving gear set comprises a driven gear mounted on said gear shaft, a driving gear wheel meshed with said driven gear, two transmission gears meshed with said driving gear wheel at two opposite lateral sides, two guide rods respectively perpendicularly connected to said two transmission gears, two barrels respectively coupled to said guide rods, an arched connection bar connected between said two barrels and a fishing line guide slot formed in said arched connection bar.

14. The spinning reel as claimed in claim 13, wherein said driving gear set further comprises a driving rod perpendicularly fixedly connected to said driving gear wheel; said handle comprises a plurality of nuts disposed at different locations for selectively fastening to said driving rod to adjust the radius of rotation of said handle and a lock member for locking the connection between the selected nut said driving rod.

15. The spinning reel as claimed in claim 1, wherein said base unit further comprises two caps respectively capped on the left and right sides of said holder base, said caps each comprising a positioning rod respectively aimed at the two axle holes of said holder base; said transmission shafts are respectively mounted with a spring member and pivotally coupled to the positioning rods of said caps.

* * * * *